United States Patent [19]

Wild et al.

[11] Patent Number: 4,996,377

[45] Date of Patent: Feb. 26, 1991

[54] PREPARATION OF ALIPHATICALLY SUBSTITUTED FLUOROBENZENES

[75] Inventors: Jochen Wild, Deidesheim; Albrecht Harreus, Ludwigshafen; Norbert Goetz, Worms, all of Fed. Rep. of Germany

[73] Assignee: BASF Aktiengesellschaft, Ludwigshafen, Fed. Rep. of Germany

[21] Appl. No.: 482,646

[22] Filed: Feb. 21, 1990

[30] Foreign Application Priority Data

Mar. 22, 1989 [DE] Fed. Rep. of Germany ....... 3909486

[51] Int. Cl.$^5$ .................... C07C 17/22; C07C 25/13; C07C 25/18
[52] U.S. Cl. .................................. 570/141; 568/731; 568/743; 568/775; 570/127; 570/129
[58] Field of Search ............................ 570/141

[56] References Cited

U.S. PATENT DOCUMENTS

| | | | |
|---|---|---|---|
| 2,563,796 | 8/1951 | Shenk et al. | 570/141 |
| 2,606,183 | 8/1952 | Head et al. | 570/141 |
| 3,678,113 | 7/1972 | Klopfer | 260/578 |
| 4,075,252 | 2/1978 | Boudakian | 260/649 F |
| 4,429,155 | 1/1984 | Goetz et al. | 564/402 |
| 4,912,268 | 3/1990 | Krackoo et al. | 570/141 |

FOREIGN PATENT DOCUMENTS

| | | | |
|---|---|---|---|
| 100120 | 2/1984 | European Pat. Off. | 570/141 |
| 330420 | 8/1989 | European Pat. Off. | |
| 2732604 | 6/1980 | Fed. Rep. of Germany. | |
| 3309354 | of 1984 | Fed. Rep. of Germany. | |
| 263518 | 6/1986 | German Democratic Rep. | |

OTHER PUBLICATIONS

The Journal of Organic Chemistry, vol. 26, (1961); pp. 919-923.
Roe, Organic Reactions, vol. V, Chapter 4.
Houben-Weyl, Methoden der organischen Chemie, vol. 5/3, pp. 213-245, Thieme, Stuttgart, 1962.
Schiemann/Cornils: Chemie und Technologie cyclischer Fluorverbindungen, pp. 3-25, Enke, Stuttgart, 1969.
Hudlicky: Chemistry of Organic Fluorine Compounds, pp. 160-169, Ellis Horwood, Chichester, 1976.
J. Am. Chem. Soc., 78, (1956), 6037.
J. Am. Chem., 19, (1954), 1594.
J. Org. Chem., 26, (1961), 919.
Izv. Akad. Nauk. SSR, Ser. Khim., 31, (1982), 2160≃Bull. of the Academy of Sciences of the USSR, Div. of Chem. Sciences, 31, (1982), 1910.

Primary Examiner—J. E. Evans
Attorney, Agent, or Firm—John H. Shurtleff

[57] ABSTRACT

Aliphatically substituted fluorobenzenes of the general formula I

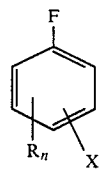

where R is an aliphatic or cycloaliphatic radical, n is 2, 3 or 4 and X is hydrogen, fluorine, chlorine or bromine, are prepared by diazotization of the corresponding aniline derivative of the general formula II

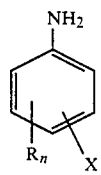

in the presence of tetrafluoboric acid and decomposition of the resulting diazonium tetrafluoborate of the general formula III

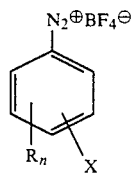

by a process in which the decomposition reaction is carried out simultaneously with the diazotization reaction, in the presence of elemental copper and/or copper(I) and/or copper(II) salts and at from −15° to 80° C.

4 Claims, No Drawings

PREPARATION OF ALIPHATICALLY SUBSTITUTED FLUOROBENZENES

The present invention relates to a process for the preparation of aliphatically substituted fluorobenzenes of the general formula I

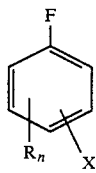

where R is an aliphatic or cycloaliphatic radical, n is 2, 3 or 4 and X is hydrogen, fluorine, chlorine or bromine, by diazotization of the corresponding aniline derivative of the general formula II

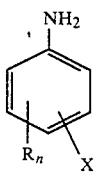

in the presence of tetrafluoboric acid and decomposition of the resulting diazonium tetrafluoborates of the general formula III

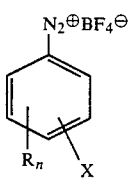

For the synthesis of the alkylfluorobenzenes of the general formula I, in general the diazonium tetrafluoborates III are produced by stepwise diazotization of the aniline derivatives of the formula II, and the said tetrafluoborates III, if necessary after isolation and drying, are decomposed thermally to the fluorobenzenes I. This procedure, together with its variants, is known as the Balz-Schiemann reaction (for reviews, see Roe, Organic Reactions, Vol. V, Chapter 4; Houben-Weyl, Methoden der organischen Chemie, Vol. 5/3, pages 213–245, Thieme, Stuttgart 1962; Schiemann/Cornils: Chemie und Technologie cyclischer Fluorverbindungen, pages 3–25, Enke, Stuttgart 1969; Hudlicky: Chemistry of Organic Fluorine Compounds, pages 160–169, Ellis Horwood, Chichester 1976).

A variant of the Balz-Schiemann reaction, in which the decomposition of the diazonium tetrafluoborates III is catalyzed by copper powder or copper salts, has been introduced by Bergmann et al. (J. Am. Chem. Soc. 78 (1956), 6037; J. Org. Chem. 19 (1954), 1594; J. Org. Chem. 26 (1961), 919). In this procedure, the diazonium tetrafluoborates III are first prepared by diazotization, isolated, and decomposed in aqueous acetone or, if the diazonium tetrafluoborates are soluble in the medium of the diazotization reaction, in this solution by the addition of the copper catalysts.

Although the Bergmann variant has a number of advantages over the conventional Balz-Schiemann reaction (for example, the decomposition temperature of the diazonium salts is substantially reduced by the addition of copper), it cannot be scaled up economically to the industrial scale, for several reasons:

1. Isolation of the diazonium tetrafluoborates III from the medium of the diazotization reaction and separate decomposition of these salts are uneconomical.
2. If the diazonium tetrafluoborates III are sparingly soluble compounds, which is generally the case, poorly stirrable, highly viscous suspensions of these salts are obtained. To maintain or restore the stirrability of these suspensions, large amounts of solvents have to be used, with the result that the process becomes substantially more expensive. On the one hand, the use of large amounts of solvents reduces the space-time yield and makes it necessary to employ large, expensive reactors, while on the other hand large amounts of solvents have to be worked up or disposed of.
3. Relatively large amounts of nitrogen and gaseous boron trifluoride are formed in the decomposition of the diazonium tetrafluoborates. If the decomposition of the diazonium salts is carried out in suspension or in solution, this gas evolution causes foaming of the reaction medium and thus greatly increases its volume, with the result that it is likewise necessary to use uneconomically large reactors. Since the addition of the copper catalysts may result in vigorous decomposition of the total amount of diazonium tetrafluoborates, there is the latent danger of uncontrollable foaming in this procedure too. This danger can be reduced only by operating the process at low space-time yields and therefore at high costs.

Since alkylfluorobenzenes I are important intermediates for the preparation of crop protection agents, it is an object of the present invention to provide a process for the economic and safe preparation of alkylfluorobenzenes.

We have found that this object is achieved by a process for the preparation of aliphatically substituted fluorobenzenes of the general formula I

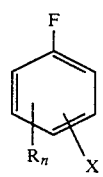

where R is an aliphatic or cycloaliphatic radical, n is 2, 3, or 4 and X is hydrogen, fluorine, chlorine or bromine, by diazotization of the corresponding aniline derivative of the general formula II

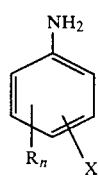

in the presence of tetrafluoboric acid and decomposition of the resulting diazonium tetrafluoborate of the general formula III

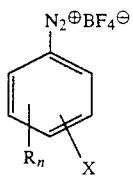

III wherein the decomposition reaction is carried out simultaneously with the diazotization reaction, in the presence of elemental copper and/or copper(I) and/or copper(II) salts and at from −15° to 80° C.

The alkylfluorobenzenes I which can advantageously be prepared by the novel process may be substituted by 2, 3 or 4 $C_1$–$C_8$-alkyl, $C_2$–$C_8$-alkenyl, $C_3$–$C_8$-cycloalkyl and/or $C_5$–$C_8$-cycloalkenyl groups R and, if required, by a fluorine, chlorine or bromine atom X.

In the novel process for the preparation of the alkylfluorobenzenes I, the diazotization reaction and the decomposition reaction are carried out side by side in the presence of elemental copper and/or copper(I) and/or copper(II) salts. Surprisingly, as a result of this measure, the above disadvantages of the conventional processes are avoided in the novel process.

The diazotization of the aniline derivatives II to the diazonium tetrafluoborates III can be carried out in a conventional manner by reacting the aniline derivative in an acidic medium with, advantageously, a stoichiometric amount of an organic or, preferably, inorganic nitrite, in particular an alkali metal nitrite, such as sodium nitrite. Since the tetrafluoborates of the corresponding diazonium compounds are required for the preparation of the alkylfluorobenzenes I, the acidic medium required for the diazotization is advantageously produced with aqueous tetrafluoboric acid. The concentration of the aqueous tetrafluoboric acid solution is in general not critical but from 1 to 60, preferably from 30 to 60, % strength by weight aqueous tetrafluoboric acid solutions are advantageously used.

According to the invention, in the present process the diazotization reaction and the decomposition reaction are carried out side by side, in a one-pot reaction, i.e. the diazonium tetrafluoborates are decomposed at the rate at which they are formed to give the alkylfluorobenzenes. This avoids accumulation of the diazonium tetrafluoborates in the reaction medium, with the adverse effects described. To ensure smooth decomposition of the diazonium tetrafluoborates, the diazotization reaction is therefore carried out in the presence of copper-containing decomposition catalysts.

Suitable decomposition catalysts are elemental copper, preferably elemental copper having a large surface area, for example copper powder, as well as copper(I) and/or copper(II) salts. The type of copper salts is in general not critical and, for example, copper(I) and/or copper(II) nitrates, acetates, halides, etc. can be used, copper(II) sulfate, copper(II) tetrafluoborate and copper(I) and/or copper(II) fluoride being preferably employed. The use of other copper halides may lead to the formation of small amounts of byproducts halogenated in the benzene nucleus. The use of catalyst mixtures of different copper salts and, if required, elemental copper is of course also possible.

The copper-containing decomposition catalysts are generally added to the reaction mixture in amounts of from 0.1 to 20 mol %, based on the aniline derivative II. In the case of smaller amounts of catalyst, the time required for the decomposition reaction is increased, and in general there are no significant advantages in using larger amounts.

The conversion of the aniline derivatives II to the fluorobenzenes I is generally carried out at from −15° to 80° C., advantageously from 0° to 60° C. The temperature of the total reaction, i.e. of the diazotization reaction and the decomposition reaction, is preferably chosen so that it is from 5° to 15° C. above the decomposition temperature of the particular diazonium tetrafluoborates, in the presence of the particular copper catalysts. Of course, the decomposition temperature of the diazonium tetrafluoborates III varies from compound to compound and may have to be determined for the individual compounds; in general, however, the diazonium salts III derived from the aniline derivatives II decompose at from 10° to 50° C.

Both the diazotization of the aniline derivatives II and the decomposition of the diazonium tetrafluoborates III are advantageously carried out in aqueous tetrafluoboric acid as a solvent. Because of the reaction procedure according to the invention, the amount of the tetrafluoboric acid serving both as reagent and as solvent can be kept small, as a rule not more than 300 ml of aqueous tetrafluoboric acid solution being required per mole of aniline derivative II. Use of larger amounts of tetrafluoboric acid is possible but has no further advantages. The addition of water-soluble, organic solvents which are inert under the reaction conditions, such as dioxane or tetrahydrofuran, to the aqueous reaction medium is also possible and may be advantageous in specific cases.

In carrying out the reaction, the aniline derivative II is usually initially taken together with the tetrafluoboric acid and the copper catalyst in the reaction vessel, in general at the reaction temperature, and the nitrite, advantageously in dissolved form, is metered in. The process can be carried out in conventional reactors, both by the batchwise and the continuous method. The alkylfluorobenzenes can be isolated from the reaction mixture by conventional methods, such as extraction, distillation or crystallization.

Surprisingly, in the novel process the alkylfluorobenzenes I can be obtained on an industrial scale in an economical, simple and convenient manner and in general without significant contamination with phenolic byproducts.

The aniline derivatives II serving as starting materials are known or are obtainable by known processes (cf. for example EP-A 53 696; US-A-3 678 113; DE-A-33 09 354 or Izv. Akad. Nauk. SSR, Ser. Khim. 31 (1982), 2160).

The alkylfluorobenzenes I are used as intermediates for the preparation of crop protection agents, for example pyrethroids, as described in O.Z. 0050/39981. For this purpose, they are converted, for example by electrochemical oxidation (cf. O.Z. 0050/39983), into the corresponding benzyl alcohols fluorinated in the nucleus, which are then esterified, for example with chrysanthemumic acid derivatives.

EXAMPLES

EXAMPLE 1

Preparation of 2-isopropyl-6-methylfluorobenzene 298 g (2 moles) of 2-isopropyl-6-methylaniline and 26 g (0.4 mole) of copper powder were added to 1.4 l of 40% strength aqueous tetrafluoboric acid at 0° C. Thereafter, a solution of 138 g (2 moles) of sodium nitrite in 550 ml of water was added dropwise at 25° C. while cooling, and the reaction mixture was stirred for 12 hours at room temperature. The reaction mixture was worked up by pouring it into 3 l of ice water and extracting the product from this mixture with methylene chloride. The organic phase was dried over sodium sulfate and evaporated down, and the crude product thus obtained was subjected to fractional distillation over a 15 cm packed column under 146 mbar.

Yield: 73%

Byproduct (2-isopropyl-6-methyl-phenol): 3.3%

EXAMPLE 2

The reaction was carried out as described in Example 1. Instead of copper powder, 25 g (0.1 mole) of copper-(II) sulfate were used.

Yield: 72% of theory.

Byproduct (2-isopropyl-6-methylphenol): 2.7%.

EXAMPLE 3

The reaction was carried out as described in Example 1. Instead of copper powder, 50 g (0.2 mole) of copper-(II) bistetrafluoborate were used.

Yield: 66% of theory.

Byproduct (2-isopropyl-6-methylphenol): 4%.

The fluorobenzenes of Examples 4 to 7 were prepared by the process of Example 1. The results of these experiments are listed in Table 1.

TABLE 1

| Example No. | Compound | Yield | Phenol formation |
|---|---|---|---|
| 4 | 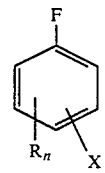 | 49% | 6.7% |
| 5 | 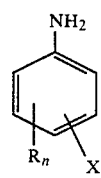 | 75% | 2.5% |
| 6 | 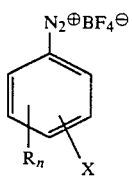 | 77% | 2.9% |

TABLE 1-continued

| Example No. | Compound | Yield | Phenol formation |
|---|---|---|---|
| 7 |  | 74% | 3.5% |

We claim:

1. A process for the preparation of an aliphatically substituted fluorobenzene of the formula I where R is an aliphatic or cycloaliphatic radical, n is 2, 3 or 4 and X is hydrogen, fluorine, chlorine or bromine, by diazotization of the corresponding aniline derivative of the formula II in the presence of tetrafluoboric acid and decomposition of the resulting diazonium tetrafluoborate of the formula III wherein the decomposition reaction is carried out simultaneously with the diazotization reaction, in the presence of elemental copper and/or copper(I) and/or copper(II) salts and at from −15° to 80° C.

2. A process as claimed in claim 1, wherein the temperature of the total reaction is chosen so that it is from 5° to 15° C. above the decomposition temperature of the diazonium tetrafluoborate III in the presence of copper catalysts.

3. A process as claimed in claim 1, wherein the reaction is carried out in an aqueous medium.

4. A process as claimed in claim 1, wherein R is $C_1$-$C_8$-alkyl, $C_2$-$C_8$-alkenyl, $C_3$-$C_8$-cycloalkyl and/or $C_5$-$C_8$-cycloalkenyl.